(12) United States Patent
Fletcher-Haynes et al.

(10) Patent No.: US 7,430,478 B2
(45) Date of Patent: Sep. 30, 2008

(54) BLOOD PROCESSING INFORMATION SYSTEM WITH BLOOD LOSS EQUIVALENCY TRACKING

(75) Inventors: Peter Fletcher-Haynes, Denver, CO (US); Christopher Fletcher, Superior, CO (US); Scott Butzke, Littleton, CO (US); Allan Gallano, Highlands Ranch, CO (US)

(73) Assignee: Caridian BCT, Inc., Lakewood, CO (US)

( * ) Notice: Subject to any disclaimer, the term of this patent is extended or adjusted under 35 U.S.C. 154(b) by 367 days.

(21) Appl. No.: 10/908,227

(22) Filed: May 3, 2005

(65) Prior Publication Data

US 2005/0209883 A1 Sep. 22, 2005

Related U.S. Application Data

(63) Continuation-in-part of application No. 09/797,325, filed on Mar. 1, 2001, now Pat. No. 7,072,769.

(60) Provisional application No. 60/186,123, filed on Mar. 1, 2000.

(51) Int. Cl.
*G06F 15/00* (2006.01)
(52) U.S. Cl. .................................. 702/21; 600/300
(58) Field of Classification Search .............. 702/21, 702/30, 31, 32, 23, 182–185; 382/133, 134; 600/300
See application file for complete search history.

(56) References Cited

U.S. PATENT DOCUMENTS

| | | | |
|---|---|---|---|
| 3,957,197 A | 5/1976 | Sartory et al. | |
| 4,299,218 A | 11/1981 | Knigge et al. | |
| 4,379,452 A | 4/1983 | DeVries | |
| 4,447,191 A | 5/1984 | Bilstad et al. | |
| 4,457,750 A | 7/1984 | Hill | |
| 4,458,539 A | 7/1984 | Bilstad et al. | |
| 4,481,827 A | 11/1984 | Bilstad et al. | |
| 4,526,515 A | 7/1985 | DeVries | |
| 4,526,574 A | 7/1985 | Pekkarinen | |
| 4,582,598 A | 4/1986 | Bilstad et al. | |
| 4,637,813 A | 1/1987 | DeVries | |
| 4,657,529 A | 4/1987 | Prince et al. | |
| 4,851,126 A | 7/1989 | Schoendorfer | |
| 4,898,675 A | 2/1990 | Lavender | |
| 4,968,295 A | 11/1990 | Neumann | |

(Continued)

FOREIGN PATENT DOCUMENTS

EP  0 580 299 A1  6/1993

(Continued)

*Primary Examiner*—Edward Raymond
(74) *Attorney, Agent, or Firm*—John R. Merkling; Edna M. O'Connor; Laura B. Hrciniegc

(57) ABSTRACT

A blood component collection system with data manipulation and optimization capabilities. The system comprises a central database, a data manipulation device, and a communication subsystem connected to the central database and the data manipulation device, and one or more extracorporeal blood processing machines. The central database maintains records of total donation volumes contributed by a donor during selected time periods as communicated by the blood processing machine and as determined by the data manipulation device. The records comprise a total red blood cell donation volume and a total plasma donation volume.

36 Claims, 16 Drawing Sheets

U.S. PATENT DOCUMENTS

| | | | |
|---|---|---|---|
| 4,994,188 A | 2/1991 | Prince | |
| 5,015,226 A | 5/1991 | Polaschegg | |
| 5,024,231 A | 6/1991 | Feldschuh et al. | |
| 5,171,456 A | 12/1992 | Hwang et al. | |
| 5,178,603 A | 1/1993 | Prince | |
| 5,200,090 A | 4/1993 | Ford et al. | |
| 5,232,437 A | 8/1993 | Lysaght et al. | |
| 5,298,171 A | 3/1994 | Biesel | |
| 5,324,422 A | 6/1994 | Colleran et al. | |
| 5,346,472 A | 9/1994 | Keshaviah et al. | |
| 5,360,542 A | 11/1994 | Williamson, IV et al. | |
| 5,370,802 A | 12/1994 | Brown | |
| 5,427,695 A | 6/1995 | Brown | |
| 5,494,578 A | 2/1996 | Brown et al. | |
| 5,496,265 A | 3/1996 | Langley et al. | |
| 5,529,691 A | 6/1996 | Brown | |
| 5,536,237 A | 7/1996 | Prince et al. | |
| 5,549,834 A | 8/1996 | Brown | |
| 5,556,749 A | 9/1996 | Mitsuhashi et al. | |
| 5,573,678 A | 11/1996 | Brown et al. | |
| 5,628,915 A | 5/1997 | Brown et al. | |
| 5,632,893 A | 5/1997 | Brown et al. | |
| 5,637,082 A | 6/1997 | Pages et al. | |
| 5,639,382 A | 6/1997 | Brown | |
| 5,641,414 A | 6/1997 | Brown | |
| 5,656,163 A | 8/1997 | Brown | |
| 5,658,240 A | 8/1997 | Urdahl et al. | |
| 5,676,841 A | 10/1997 | Brown | |
| 5,681,273 A | 10/1997 | Brown | |
| 5,693,232 A | 12/1997 | Brown et al. | |
| 5,712,798 A | 1/1998 | Langley et al. | |
| 5,721,676 A | 2/1998 | Bolden et al. | |
| 5,730,883 A | 3/1998 | Brown | |
| 5,759,413 A | 6/1998 | Brown | |
| 5,769,811 A | 6/1998 | Stacey et al. | |
| 5,792,372 A | 8/1998 | Brown et al. | |
| 5,793,969 A | 8/1998 | Kamentsky et al. | |
| 5,807,492 A | 9/1998 | Brown et al. | |
| 5,812,419 A | 9/1998 | Chupp et al. | |
| 5,833,866 A | 11/1998 | Brown | |
| 5,915,240 A * | 6/1999 | Karpf | 705/2 |
| 5,930,791 A | 7/1999 | Leu | |
| 5,956,023 A | 9/1999 | Lyle et al. | |
| 5,964,724 A | 10/1999 | Rivera et al. | |
| 5,970,423 A | 10/1999 | Langley et al. | |
| 5,993,370 A | 11/1999 | Brown et al. | |
| 6,007,725 A | 12/1999 | Brown | |
| 6,027,657 A | 2/2000 | Min et al. | |
| 6,046,761 A | 4/2000 | Echerer | |
| 6,059,979 A | 5/2000 | Brown | |
| 6,071,421 A | 6/2000 | Brown | |
| 6,080,322 A | 6/2000 | Deniega et al. | |
| 6,113,554 A | 9/2000 | Gilcher et al. | |
| 6,233,525 B1 | 5/2001 | Langley et al. | |
| 6,251,284 B1 * | 6/2001 | Bischof et al. | 210/739 |
| 6,256,643 B1 | 7/2001 | Cork et al. | |
| 6,581,011 B1 | 6/2003 | Johnson et al. | |
| 6,673,314 B1 * | 1/2004 | Burbank et al. | 422/44 |
| 6,730,054 B2 | 5/2004 | Pierce et al. | |

FOREIGN PATENT DOCUMENTS

| | | |
|---|---|---|
| WO | WO 84/00112 | 1/1984 |
| WO | WO 00/78374 A1 | 12/2000 |
| WO | WO 01/02979 A2 | 1/2001 |

* cited by examiner

Donor Entry/Edit — 221

Donor
Identification

| Last Name | First Name | Middle Initial |
|---|---|---|
| John | Doe | L |

Donor ID: .335566

[Edit Donor Name]
[Edit Donor ID]

— 222

Demographics | History | Comments | Allergies | Status | Blood Loss History | Procedure History — 231

| | |
|---|---|
| National ID Number | 123-22-444 |
| Address | 781 Locklear Avenue |
| City | Sarasota |
| State/Province | FL |
| Postal Code | |
| Telephone Number | 941 955 9661 |

[Alternate Numbers]

— 224

[Remove]

[OK] — 230
[Cancel] — 228
[Apply] — 229
[Help] — 227

Donor Entry/Edit

Identification

| Last Name | First Name | Middle Initial |
|---|---|---|
| Wright | Joseph | L |

Donor ID: 335566

Edit Donor Name
Edit Donor ID

Demographics | General | History | Comments | Allergies | Status | Blood Loss History | Procedure History

281

Donor Status
○ Active
○ Inactive

Donor Category: Whole Blood Donor ▽

Donor Since Date: ☑ 12/3/04 ▽

Last Visit Date: ☑ 12/3/04 ▽

Last Procedure Date: ☑ 12/3/04 ▽

Last Contact Date: ☑ 12/3/04 ▽

Remove

OK | Cancel | Apply | Help

Donor Entry/Edit

Donor
Identification

| Last Name | First Name | Middle Initial |
|---|---|---|
| John | Doe | L |

Donor ID: 335566

[Edit Donor Name]
[Edit Donor ID]

Demographics | General | History | Comments | Allergies | Status | Blood Loss History | Procedure History

12 Month History  Total Blood Loss = 20

| Procedure Date | Product RBC | Sample RBC | Residual RBC | Other RBC | Product Plasma |
|---|---|---|---|---|---|
| 2/2/04 | 0 | 0 | 0 | 0 | 0 |
| 2/4/04 | 0 | 0 | 0 | 0 | 0 |
| 12/3/04 | 0 | 0 | 0 | 0 | 0 |
| 12/6/04 | 0 | 0 | 0 | 0 | 0 |
| 12/6/04 | 0 | 0 | 0 | 0 | 0 |
| 12/7/04 | 0 | 0 | 0 | 0 | 0 |
| 12/7/04 | 0 | 0 | 0 | 0 | 0 |
| 12/8/04 | 0 | 0 | 0 | 0 | 0 |

[OK] [Cancel] [Apply] [Help]

[Remove]

Figure 2E

Donor Entry/Edit — 221

Donor
Identification

| Last Name | First Name | Middle Initial |
|-----------|------------|----------------|
| John | Doe | L |

Donor ID: 335566

[Edit Donor Name]
[Edit Donor ID]

Tabs: Demographics | General | History | Comments | Allergies | Status | Blood Loss History | Procedure History — 299

| Procedure Date | Platelet Yield | Plasma Volume | RBC Volume |
|----------------|----------------|---------------|------------|
| 2/2/04 | 0 | 0 | 0 |
| 2/4/04 | 0 | 0 | 0 |
| 12/3/04 | 0 | 0 | 0 |
| 12/6/04 | 0 | 0 | 0 |
| 12/6/04 | 0 | 0 | 0 |
| 12/7/04 | 0 | 0 | 0 |
| 12/7/04 | 0 | 0 | 0 |
| 12/8/04 | 0 | 0 | 0 |
| 12/8/04 | 0 | 0 | 0 |
| 12/10/04 | 0 | 0 | 0 |

[Remove]

[OK] [Cancel] [Apply] [Help]

Finalize Procedure Information — 621

| | | | |
|---|---|---|---|
| Unit Number | 09310 | Donor ID | 445-556-3355 |
| Machine ID | TR6 | Donor Name | Jane Doe |
| Procedure Date | 02/03/04 | End Time | 10:15 am |

Tabs: Supplies | Operators | Donor Information | Record Status | Procedure Log | Run Summary | Blood Loss — 681

Estimated Product Information

| Product | Volume (ml) | AC Volume (ml) | Yield |
|---|---|---|---|
| Platelet | 0 | 0 | 0 |
| Plasma | 0 | 0 | 0 |
| RBC | 0 | 0 | 0 |

Total AC Used (ml): 0
Actual AC to Donor (ml): 0
Blood Volume Processed (ml): 0

Post-procedure Counts
Hematocrit: 0
Platelet: 0

[ Help ]   [ Apply ]   [ OK ] — 622   [ Cancel ]

Finalize Procedure Information

Unit Number: 09310
Machine ID: TR6
Procedure Date: 02/03/04

Donor ID: 445-556-3355
Donor Name: Jane Doe
End Time: 10:15 am

Tabs: Supplies | Operators | Donor Information | Record Status | Procedure Log | Run Summary | Blood Loss — 691

| Description | Plasma (ml) | RBC (ml) |
|---|---|---|
| Product | 0 | 0 |
| Tubing Set Residual | 0 | 0 |
| Blood Sample | 0 | 0 |
| Other | | 0 |

☐ Donor Completed Rinseback

[Help] [Apply] [OK] — 622 [Cancel]

BLOOD PROCESSING INFORMATION SYSTEM WITH BLOOD LOSS EQUIVALENCY TRACKING

This is a continuation-in-part of U.S. patent application Ser. No. 09/797,325 filed Mar. 1, 2001, which claims priority of U.S. Provisional Application 60/186,123, filed Mar. 1, 2000.

FIELD OF THE INVENTION

The present invention generally relates to the field of extracorporeal blood processing systems and, more particularly, to providing information management, data manipulation, or optimization capabilities for such systems.

BACKGROUND OF THE INVENTION

Blood donation and transfusion are well known. In some instances, whole blood is collected. In others, selected blood components are separated from donated blood for the therapeutic benefits of particular blood components. Blood components used in many separation and collection technologies include platelets, red blood cells, white blood cells, stem cells and plasma.

In harvesting blood components, blood is removed from a donor through a needle assembly and then is processed by centrifugation or other appropriate separation techniques to isolate and collect the desired components. This procedure is often carried out very effectively by apheresis wherein blood is removed from a donor and processed in a disposable extracorporeal fluid circuit to obtain the desired components and the uncollected components are thereafter returned to the donor. Two illustrative blood component collection systems, which provide for this type of blood component collection procedure, are the COBE Spectra (trademark) and Trima (trademark) apheresis systems, which are commercially available from the assignee of the present application. Other illustrative devices, which also perform similar procedures, include the Haemonetics MCS or MCS+, the Baxter Amicus, and the CS-3000 apheresis machines.

Donor characteristics (supply) and patient needs (demand) are important factors in the ultimate usefulness of collected blood components. Donors are "screened" when they appear for a donation based on their medical status (e.g. blood pressure) and personal history (e.g. contact with diseases). Donor "eligibility", based on the donor record of blood donation or other blood loss, is often determined by regulatory issues or blood center rules, which may limit total periodic (e.g., monthly or yearly) blood component losses from individual donors or may set minimum interval periods between donation occurrences. A large number of variables must be simultaneously managed in order to meet the blood bank collection goals and rules, which will thus also satisfy the needs of a hospital or other customer. Computerized information systems are tools that are beginning to prove useful in assisting in controlling parts of blood collection processes. Such an extracorporeal blood processing information management system is disclosed in U.S. patent application Ser. No. 09/797,325, filed Mar. 1, 2001; Patent Cooperation Treaty application serial. No. PCT/US01/06696, filed Mar. 2, 2001 and Patent Cooperation Treaty application serial. No. PCT/US01/20540, filed Jun. 25, 2001, each of which is incorporated herein by reference.

Total periodic loss of plasma and total periodic loss of red blood cells (RBC's) are donor eligibility requirements usually set by government regulations or blood center rules. Frequently, however, a donor's actual loss of each of these blood components is unknown. It is desirable, nevertheless, that a blood processing information management system account for total periodic blood component loss restrictions.

SUMMARY OF THE INVENTION

The present invention relates to a blood component collection system with management capabilities including data manipulation and optimization principles. A software application may be run with one or more hardware devices including, for example, a data input device, a data storage device, a data manipulation device, and one or more communications devices, which may connect such input, storage, or manipulation devices to each other and to at least one blood component separation or collection machine, including apheresis or other types of blood processing machines.

An important purpose of the present system is to address various challenges in the area of blood donation management including improved donor eligibility. Donor eligibility may be improved through procedure customization and optimization. Each donation may be customized by this system to account for the current needs of a blood center and optimized by what each particular donor is eligible for or capable of donating. This allows the operator to determine what product or combination of products will best be collected from a particular donor even before the donor is connected to the blood processing machine. It also allows the blood center operators to determine what tubing set may be required for the donation, also before connection of the donor to the particular blood processing machine. With this information the blood center can avoid wasting tubing sets and reduce incomplete procedures. The blood centers may also optimize the use of donors, that is, it may actively identify and contact eligible donors. Donor eligibility is determined, at minimum, by the interval between donations, the number of donations previously given, the blood component loss over a period of time, and other donor eligibility issues. In particular, in the present invention, blood component loss qualifications are maintained, even if actual blood component loss is not known.

To implement the above and other features of the present invention, a central computational and data storage system is established that communicates with each of one or more blood processing machines, preferably apheresis or other separation machines. Each blood processing machine receives both temporary and permanent information, such as procedural lists and priority information, donor vital information (height, weight, gender, blood component pre-counts and total blood volume), as well as donor identification. The centralized system may also retrieve from each blood processing machine information regarding conditions such as alarms, procedure adjustments, and run progress (product collection information) for monitoring purposes. It may also retrieve end-of-run summary information and run logs after each procedure is complete. The centralized system can use data from the blood processing devices to detect and isolate potential maintenance problems before they manifest themselves to the blood center. These potential problems can be reported so that preventive maintenance may be performed. The central database provides the system with the capability of storing and maintaining data relevant to the entire blood component collection process, such as donor demographic information, machine configuration information, run information and lab result information. Lab data can also be entered to complete the product collection run record.

The present system may use prediction algorithms like those used in the Trima or Spectra apheresis machines. The prediction algorithms can be applied to individual donors, to a reference donor list, or to ranges of donors within the database. This capability is helpful to predetermine donor eligibility for specific product collections, and what products would be available given specific apheresis machine configuration settings. As mentioned above, eligibility may be derived not only from such factors as donor height, weight, and gender, but also from total periodic blood component losses (e.g., yearly cell losses) per donor, time interval between donation events per donor, and frequency of donations.

In the system described herein, records for a donor's total annual donation or loss both of red blood cells and of plasma are maintained. Where a donation comprises a donation of either red blood cells or plasma by apheresis, the actual amount of extracted blood component is recorded. Where a donation of whole blood is made, and the donor's actual hematocrit is known, a portion of the donation volume is attributed to red blood cells and another portion is attributed to plasma, based on the actual hematocrit. Where the actual hematocrit of the whole blood donation is not known, a portion of the donation volume is attributed to red blood cells based on a maximum feasible hematocrit and another portion is attributed to plasma based on a minimum feasible hematocrit. This provides blood loss equivalency tracking. In all cases, the desired standards set by government regulation or blood center rule are met or exceeded. A donor can safely donate either whole blood or blood components at appropriate times while maintaining the standards for blood donation eligibility.

These and other features of the present invention can be better understood from the following detailed description of a preferred embodiment of the present invention taken in conjunction with the accompanying drawings, which are briefly described below.

BRIEF DESCRIPTION OF THE DRAWINGS

FIGS. 2A-2F are display screen depictions of data entry, retrieval or manipulation display pages for use in accordance with the present invention.

FIGS. 5A and 5B are display screen depictions of reports produced after a blood collection procedure.

DETAILED DESCRIPTION

The present invention will be described with reference to the accompanying drawings. One application of the present invention involves one or more blood component collection systems that separate, remove, or collect at least one type of blood component (platelets, red blood cells, stem cells, white blood cells, plasma) from a source of whole blood (a donor or a bag of whole blood).

Figure 1A:
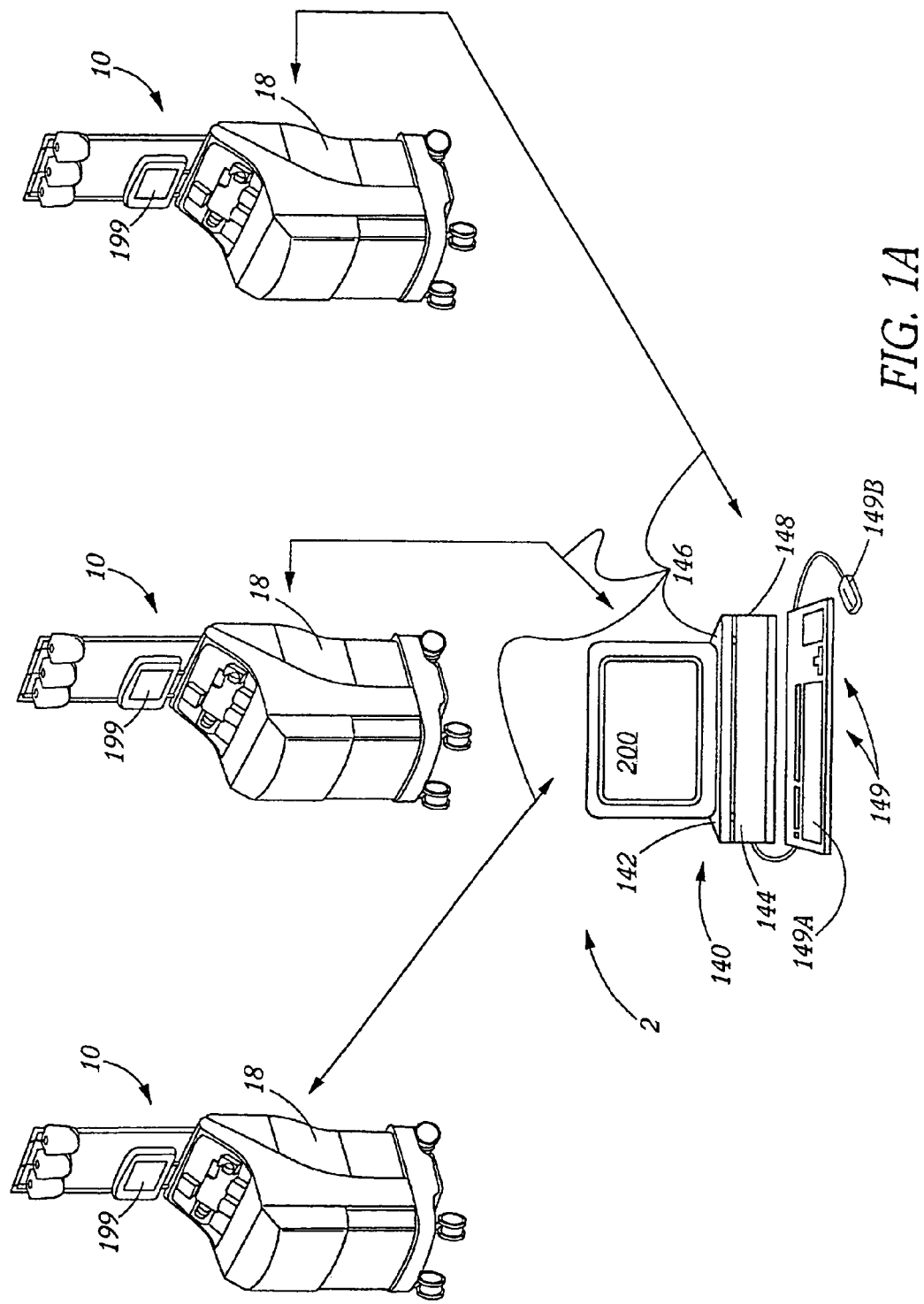
FIG. 1A is a schematic representation of a blood processing information management system in accordance with principles of the present invention.

Referring to FIG. 1A, a first representation of a blood processing system is shown as including a blood component collection and information management system generally identified by the reference numeral 2. The system 2 may typically be implemented at a blood bank (not shown in FIG. 1A, but see blood center 1000 in FIG. 1B). The system 2 may include a substantially centralized computing and data storage assembly 140, for example, an appropriate data manipulation device or microprocessor 144 and at least one blood component processing assembly (three shown), each generally identified with reference numeral 10. Each such blood processing assembly 10 includes a blood component separation and collection device 18 as an integral part thereof. The computing and data storage assembly 140 (or at least a portion thereof) and the associated blood component separation and collection assemblies 10 are appropriately interfaced with each other in data communication relationship as will be described, but may be physically separate from each other. That is, component separation or collection, data communication, retrieval, manipulation, and optimization procedures are not limited to being performed at any particular physical location of apheresis, separation, or collection machines(s) 10 relative to the assembly 140. Furthermore, data entry, manipulation and storage may still be performed on each machine 10 using, for example, respective interfaces, which here are shown as touch screen input-output devices 199.

Figure 1B:
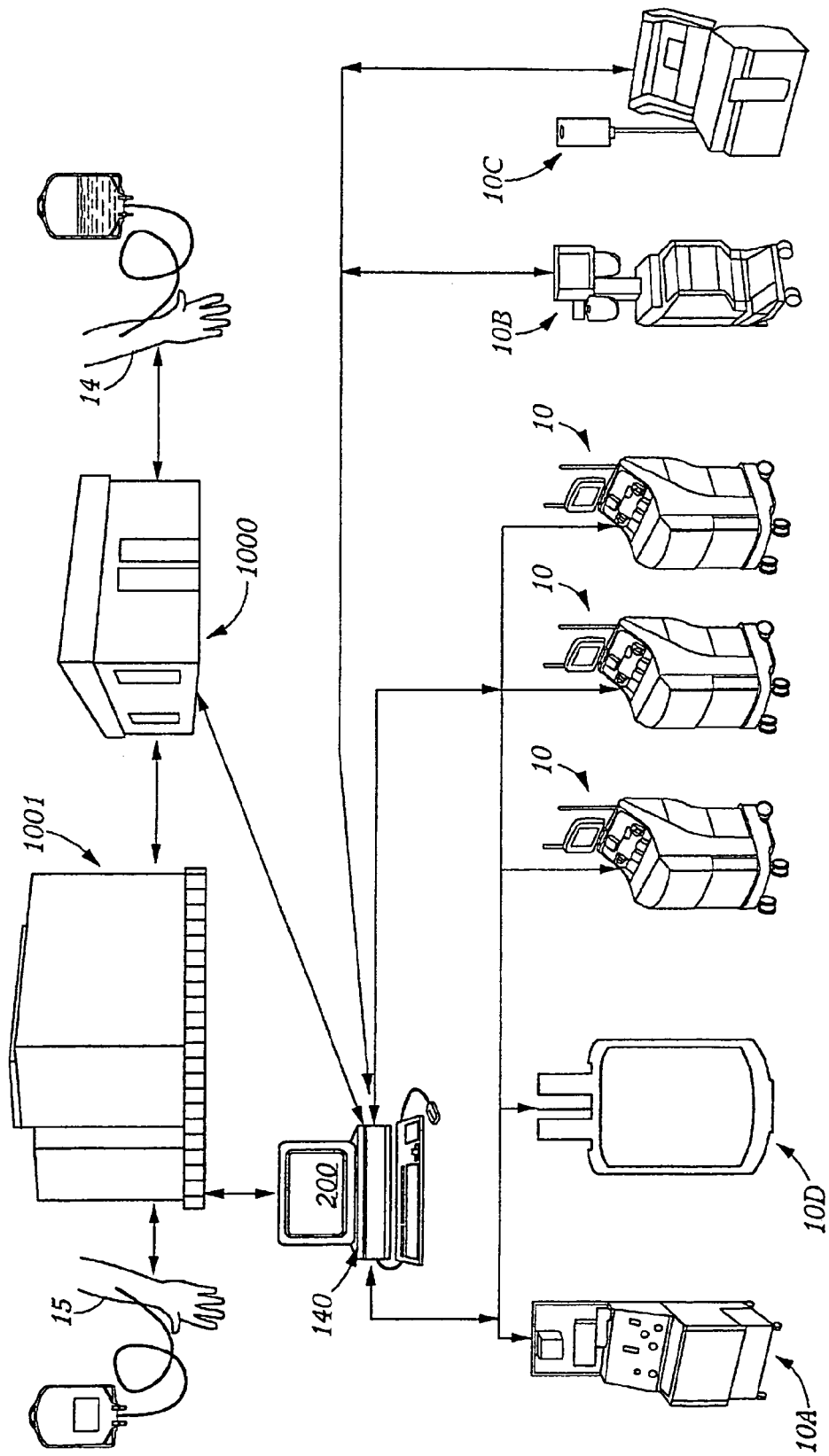
FIG. 1B is another schematic representation of a blood processing information management system in accordance with principles of the present invention.

In FIG. 1B, the computing and data storage assembly 140 is shown schematically disposed in communicative relationship with various types of blood component separation and collection machine assemblies 10, as well as with either a discrete blood center information system within a blood center 1000 or a hospital information system within a hospital 1001, or both. Thus, the computing and data storage assembly 140 may make use of multiple communication connections, including satellite or wide area networks, for example. Although connections to Trima apheresis machines 10 are shown and described throughout, these are intended as exemplars only. As shown in FIG. 1B, connections can be made to numerous other machine types as well, such as COBE Spectra apheresis machines 10A or Baxter International, Inc. Amicus (trademark) machine 10B and Haemonetics Corporation MCS+ machine 10C, shown in FIG. 1B. Use with a more traditional manual whole blood collection system is also shown schematically in FIG. 1B, generally identified by the reference numeral 10D and by symbolic representation of whole blood donations at numerals 14 and 15, therein. Thus, this system is intended to and will operate with various apheresis as well as whole blood collection and separation systems.

The computing and data storage assembly 140 may include, as shown schematically in FIG. 1A, a personal computer 148 with data input devices 149. Such devices 149 may include a keyboard 149A, a mouse 149B, or, if desired, devices such as a barcode reader (not shown), or a digital camera (not shown) or a display monitor and screen 200. The assembly 140 may include a data manipulation device or microprocessor 144, disposed within assembly 140 in FIG. 1A. Data manipulation device 144 may be an appropriate processor for a microcomputer or personal computer including an operating system and may further include other devices and software, whether resident in the processor or in other associated memory devices. The computing and data storage assembly 140 uses a storage medium for data storage. Hardware and software for data communication between various elements of assembly 140, as well as between assembly 140 and external devices, some of which are like those shown in FIGS. 1A and 1B, are hereafter referred to as a communication subsystem 146. Subsystem 146 may also be mainly disposed in the assembly 140 or may be physically separate therefrom so long as it provides data communication functions.

The assembly 140 may input and maintain donor related data functions, and also prepare an initial procedure order for a donor. Additional configurations will be apparent to persons of skill in the art, for example, additional systems and system details described in U.S. patent application Ser. No. 09/797,325, Patent Cooperation Treaty application serial. No. PCT/US01/06696, and Patent Cooperation Treaty application serial No. PCT/US01/20540.

Figure 6:
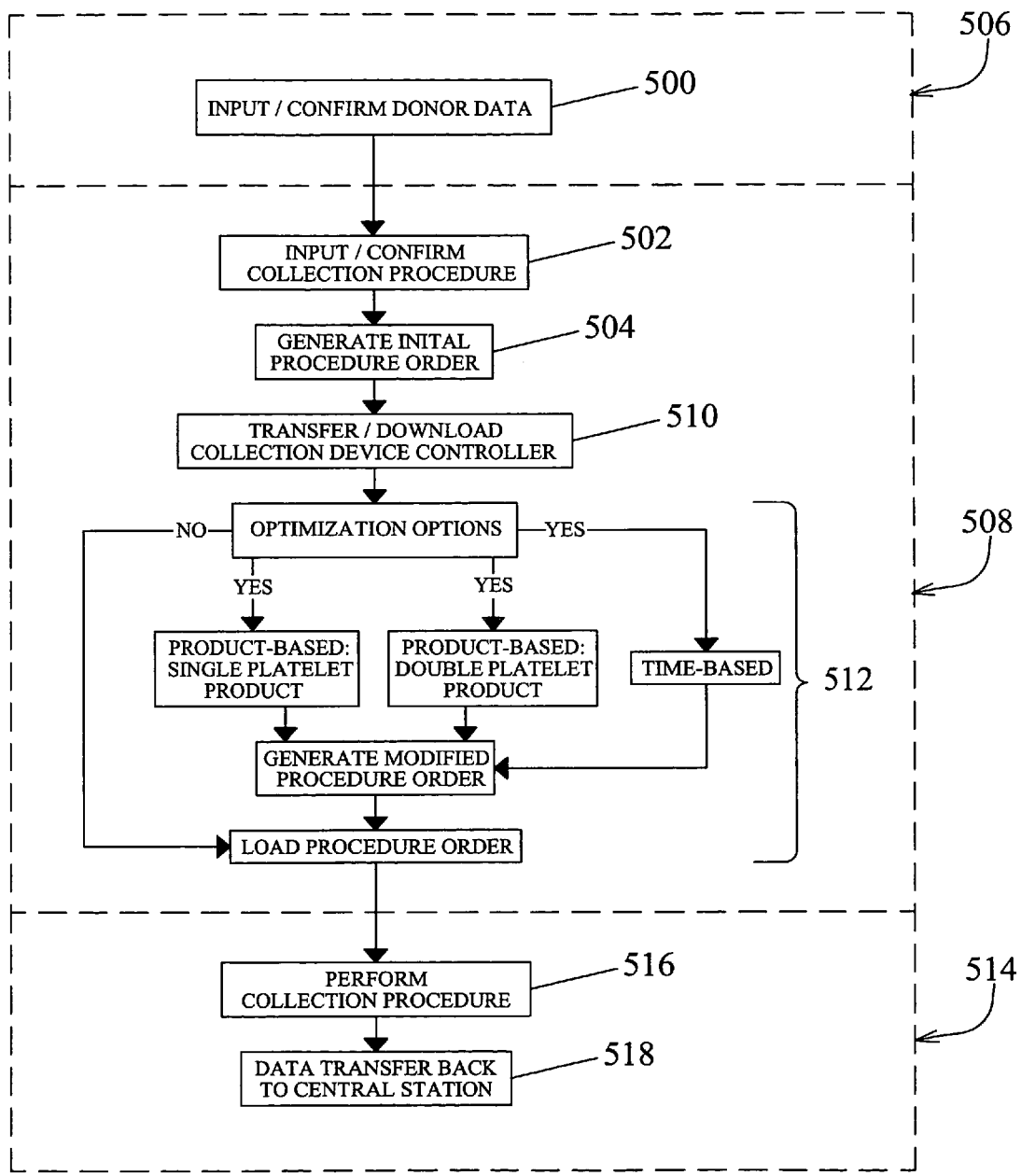
FIG. 6 is a flow chart of a blood component collection procedure utilizing principles of the present invention.

Referring now to FIG. 6, the operation of the computing and data storage assembly 140 will be described with regard to a standard exemplary procedure. The computing and data storage assembly 140 will typically be used by blood banks as the primary means for donor data input and donor data management. Information relating to a donor such as gender, height, weight, total blood volume, blood type, temperature, pressure and demographics will preferably be input 500 at the computing and data storage assembly 140, or could be easily downloaded to the computing and data storage assembly 140. Moreover, information relating to the donor's hematocrit and a blood component pre-count(such as platelet pre-count), both of which may be obtained from a donor blood sample and determined by known techniques such as cell counters, may also be entered at the computing and data storage assembly 140. In addition to donor related data, the particular type of collection procedure to be used for the donor (e.g., single needle or double needle) may be input 502 at the computing and data storage assembly 140. These also could be downloaded from another system. Based upon this information and certain site standardized conditions (e.g., total procedure time, collection efficiency, AC infusion rate), an initial procedure order is thereafter generated 504, preferably by the manipulation device 144, which specifies the various process control parameters associated with the selected collection procedure.

A more detailed description of the preferred steps relevant to the claimed invention for using the system will now be set forth. Additional steps are known from U.S. patent application Ser. No. 09/797,325. Use of the computing and data retrieval assembly is shown in more detail in U.S. Pat. Nos. 5,496,265; 5,658,240; 5,712,798; and 5,970,423, all of which being commonly assigned to the assignee of the present invention, the disclosures of which being incorporated herein in their entireties as if fully set forth here by this reference thereto.

There may be considered three main data input and verification points in a collection process. These points may be physically separate, that is, located in different areas or rooms, or merely logically separate. Privacy requirements may determine the conditions for the three points, shown logically separated in FIG. 6. At the first point, hereafter referred to as "Reception" 506, the donor is checked into the overall process. Under a scenario of data connectivity between the computing and database assembly 140 and a blood bank information system, the "Reception" room step 506 may be handled through the blood bank information system and the needed donor data may then be automatically transmitted (downloaded or uploaded or otherwise) into the assembly 140 as described above. With this connectivity between the blood center information system and the assembly 140, the historical donor data may also be called up and the donor may then be assigned to the second room, hereinafter also called the "Screening Room" 508. In the screening room the donor information may be retrieved and displayed and several pieces of lab data may be input for purposes of selecting 512 the proper collection procedure to be performed. A donation unit number may also be assigned at this point. The assembly 140 may, but preferably does not, hold confidential donor information influencing potential deferral; this information would preferably reside only in the blood bank information system. The assembly 140 is preferably only concerned with the collection process. In either the "screening room" or a third room, hereinafter also called the "Donation Room" 514, the donor may be assigned 516 to a particular apheresis machine. The procedures performed 516 in the Donation Room 514 may also include recording other data about the procedure such as recording the identification numbers associated with the disposable tubing set. Once the donor is assigned to a machine, the assembly 140 would preferably go into a monitor only mode relative to that donor and that machine for monitoring or recording 518 any or all events in the procedure.

Figure 2A:
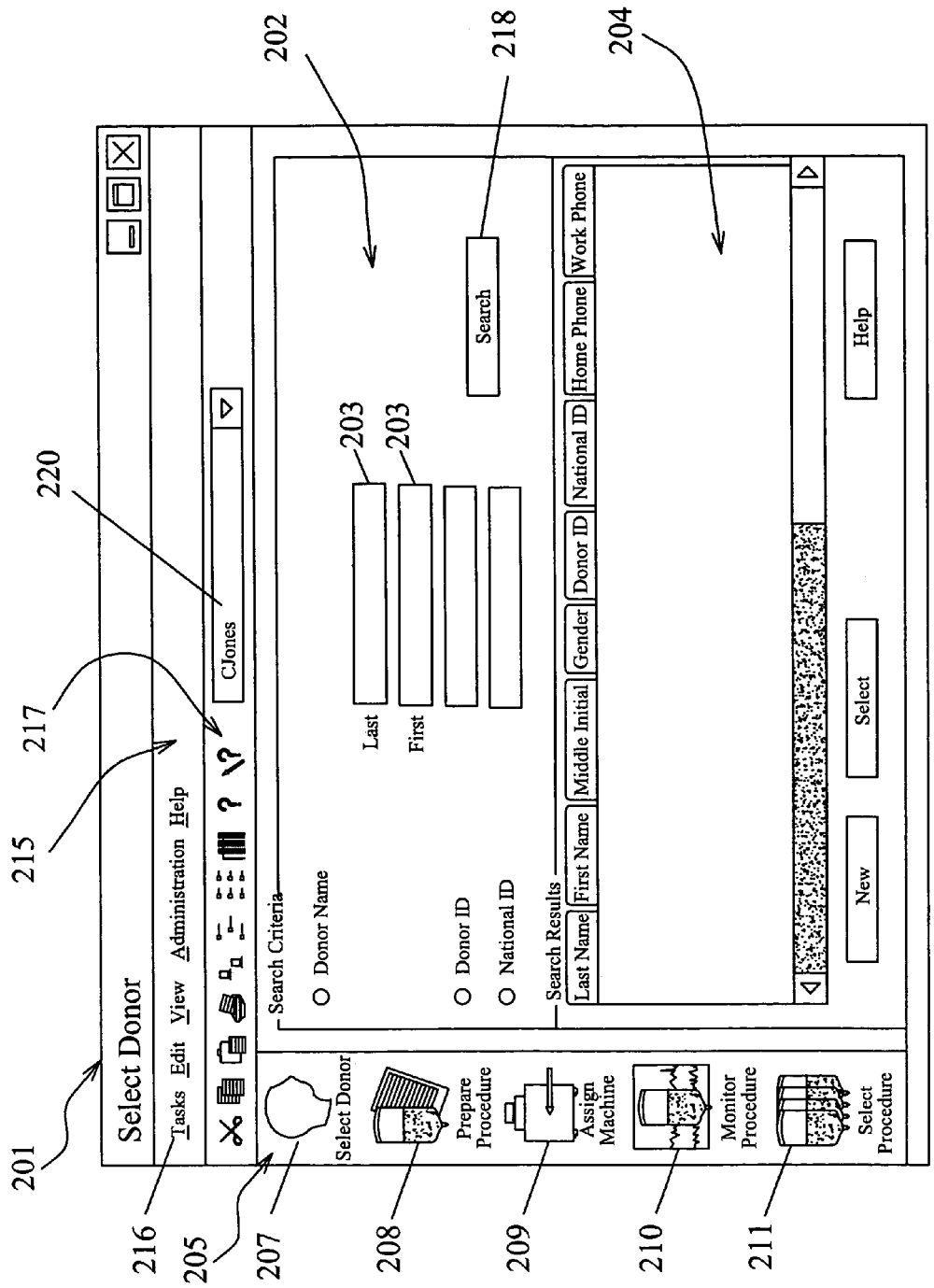
Figure 2C:
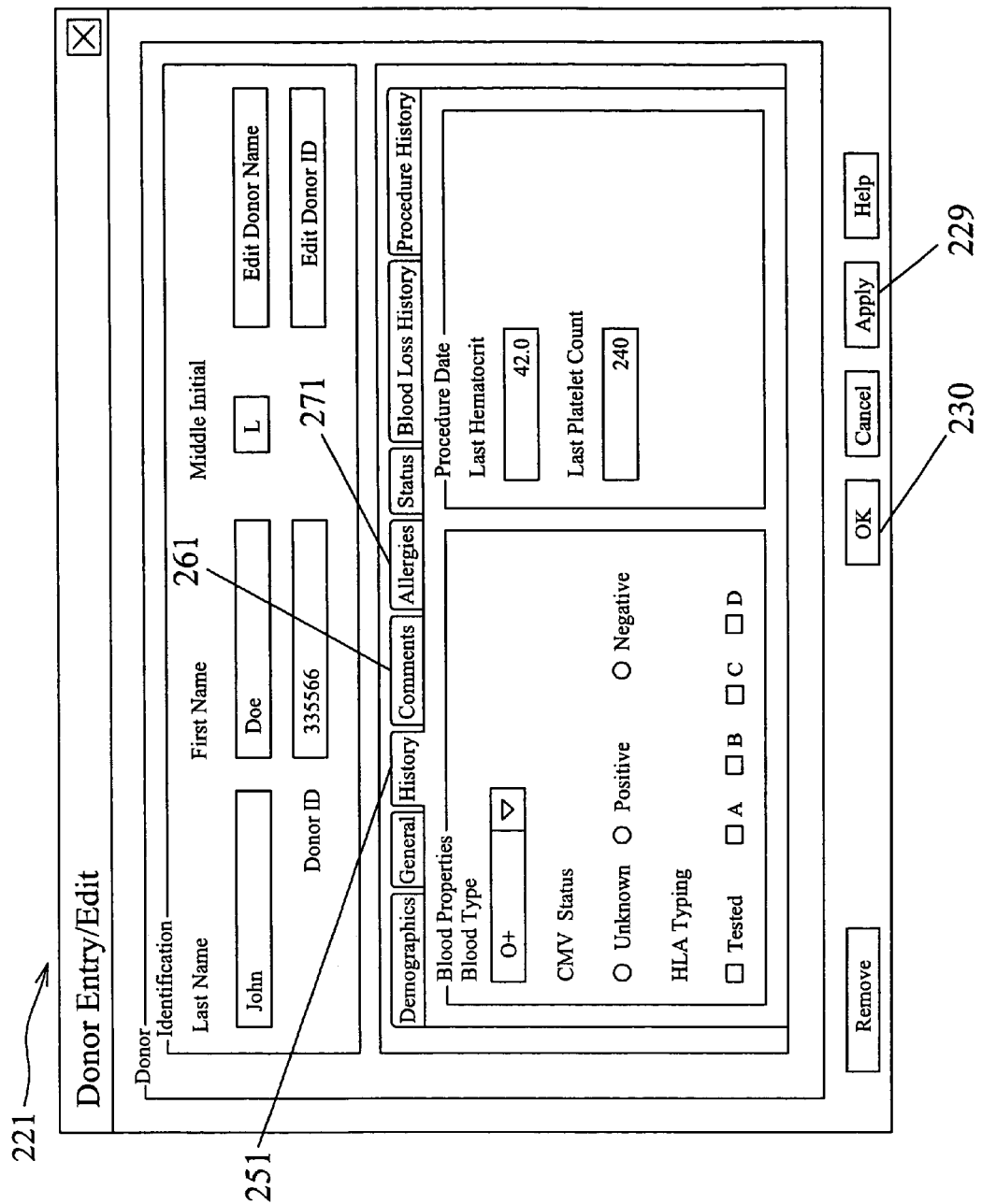

FIG. 2A depicts an exemplary display screen 201 which may be the first screen displayed on the output monitor display screen 200 (FIG. 1A) of the computing and data storage assembly 140 in connection with Reception functions. Initial donor information may be gathered in display screen 201, such as the donor's name in entry 203, or the donor's identification (ID) number or like identifier, or the donor's telephone number or other identification data. Data entry fields for these types of data may be seen in a main work area 202. Numerous other initial identifiers could be substituted. In any event, some display is preferably used as the starting point for data entry or search, if the data were previously entered or imported from another system for use with a particular donor. As shown in FIG. 2A, disposed next to the main work area 202 is a procedure icon selection area 205, which is depicted along a vertical portion of the left hand side of display 201. In it, five icons 207, 208, 209, 210, and 211 are currently shown, though either more or fewer such icons could be used as may be desired. The overall procedural flow will be set forth starting with particular reference to the procedure icon bar 205 on the left side of the display screen 201. Most of the following description flows from one procedural event to another, however, the procedures herein are not necessarily intended to rigidly follow each other sequentially, and may be performed in various orders, non-sequentially, synchronously or non-chronologically.

As an initial step or sub-procedure, the Select Donor icon 207 represents the performance of several functions. First, in a Greet Donor function, the system operator may verify or add a new donor record to the system database 142, either by data entry directly into this application or by automatic transfer of data from a discrete blood bank information system. Thus, the operator may perform Donor Entry functions to enter or modify a donor record in the database. A data entry could be tied to a previously populated data record and could be tied to previously entered donor demographic or physical information including height, weight and the like.

After the data entry and verification, the next general step would preferably be a Prepare Procedure for component collection, as indicated by the second icon 208 in bar 205. This involves using the Prepare Procedure sub-procedure 208 to record further donor information and select the procedure to use with the donor. Next, the operator uses the Assign Machine icon 209 to access a sub-procedure for assigning the donor to a particular apheresis collection system 10.

An optional step in the overall procedure shown in FIG. 2A by the icon 211 is the Select Procedure sub-procedure where the operator may search for and select an active, pending, or finalized procedure record. The operator will then be able to enter lab results into the record by entering procedure product volume or quality information returned from the lab. The operator may also generate reports such as procedure, donor, or production reports.

The various sub-procedures identified by the respective icons 207-211 can be selected at any time in the overall procedure to view, input or modify information. For example, the Assign Machine icon 209 could be selected at any time to view the list of available or assigned machines 10. However, certain functionalities may be unavailable if an icon 207-211 is selected without having completed a previous sub-procedure. For example, upon selection of the Assign Machine icon 209 as suggested here, the assignment function will not be available unless at least one donor has been processed though the Prepare Procedure sub-procedure 208. Similar functionalities may require pre-completed sub-procedures, thus building on previous module completion.

After log-in, an operator may select an icon from a menu list or from the left-hand procedure icon selection area or bar 205 in order to initialize the overall procedure. As an example, the operator could first select the select donor icon 207 with a computer screen cursor or pointer (not shown) and click the "enter" or mouse button (neither shown) as is known in the art of standard personal computer software applications. This selection could then bring up the illustrated display 201 for beginning a donor check-in procedure. Scanning a bar-coded donor ID could also be used to initialize the donor check-in or registration process. A few further alternatives for use in start-up (as well as throughout operation) may be found on toolbars located as shown horizontally along the upper portion of the display 201. These are toolbars like those used in Windows (trademark)-type software applications. For example, the software start-up to the initial working display may also be achieved by selecting the "Tasks" menu heading 216 in the top level menu toolbar 215 and then selecting the appropriate "open" file command (not shown) or other like commands as are generally known in the art. Or, similarly, a small icon toolbar 217 may be configured to be used for initiating software procedures, as may also be generally known in the art. Other menu headings or icons (not shown) in toolbars 215 or 217 (or otherwise, not shown) may be used for other functions in startup or otherwise.

Returning now to the main work area 202 of the display screen 201, two sub-areas 203, 204 are shown in which data may be entered or displayed. First, as shown in donor name entry 203, data concerning the identity of the donor to be checked-in may be entered in order to begin the donation process. This data entry could be by various methods, such as manual data entry, data download from a discrete data system, or barcode reading, and these data entry variations are intended to be interpreted as interchangeably usable throughout this description. The computer and data storage assembly 140 may then be made to search its database 142 (automatically upon one or more alphanumeric entries or by selection of the search button 218 by the operator) to determine whether this particular donor has been previously entered in the system. If so, the assembly 140 returns the results of that search in the search results sub-area 204.

As shown by the donor data entry screen 221 in FIG. 2B, data can be manually input into the computer and data storage assembly 140 by typing into the corresponding fields, or any appropriate data input can be performed with an alternative input system such as, for example, a bar code reader, or input from other computerized information systems. Data can be exported from a pre-existing database and information system, which may already contain the appropriate donor data. The present computer and data storage assembly 140 may be disposed in data communication relationship with one or more such pre-existing systems and the fields such as those shown in FIG. 2B, can be automatically populated from the blood center's management information system. A primary difference in creating new records versus modifying existing ones lies in the fact that the fields shown in FIG. 2B will be empty prior to entry of new record information, as opposed to having been populated by previously entered (or imported) data in the modification sense. Primarily donor identification data, such as the donor's name or ID, may be entered in the fields disposed preferably in an upper substantially fixed area 222 of screen 221. However, if this data has come from a previously entered record, the fields in area 222 are preferably "inactive" as shown by being "grayed-out." Thus, these fields would preferably not be editable directly, but would be editable otherwise as described herein. Other information about a particular donor may then be entered in corresponding fields appearing with respective tabs in the lower data area 224. For example, donor demographics information may be entered in corresponding fields under the "Demographics" tab 231 as shown in FIG. 2B. Other general information such as gender, ethnic background, or date of birth, would preferably be enterable under the "General" tab 241. Blood type, CMV (cytomegalovirus) and HLA (Human Leukocyte Antigen) type could be entered under the "History" tab 251. A "Comments" tab 261 could be selected and used for entry of comments about the donor. Allergy information could be entered or edited under an "Allergies" tab 271. Donor status data could be entered or edited under a "Status" tab 281 including such data as, for example, last procedure date, numbers of donations given, over what period of time, etc. Other tabs, such as a "Blood Loss History" tab 291 or a "Procedure History" tab 299 could also be used for separate entry of such information. Separate pop-up dialog boxes or other alternative screen styles or types (none shown) may be used for prompting for and entering these types of information.

The information shown and described here in screen 221 may be optional or mandatory, depending on the desires of the ultimate user. That is, the standard operating procedures (SOP's) of the blood center may be implemented herein to make certain information optional or mandatory, as desired. However, certain information, whether listed here (under the Donor Entry screen 221) or entered elsewhere (see the Prepare Procedure functionality, described below) may be important to the blood separation and collection assembly 10 prior to initiation or completion of a separation-collection procedure. Examples of such information may be gender, height, weight, blood type, or pre-count (platelets or hematocrit) information.

In the Demographics tab 231, the operator may enter the donor's national ID (as may be desired or applicable), address and telephone number as shown in FIG. 2B. Then, after selecting the General tab 241, the following information may preferably be entered: Gender (Male or Female, neither of which preferably selected by default); Date of Birth (which can be typed in text box or selected using pop-up calendar); Ethnic Background (preferably available via a drop-down list which is editable by selection only, and is preferably created by the System Administrator); and Donor Picture (the default is preferably a generic, genderless icon; however, if a gender is selected using one of the Gender radio buttons, this icon preferably changes to a gender-specific icon the next time the donor record is accessed, provided the operator saved the data before closing the dialog box). The operator can optionally click Update Picture to take donor's photo using an optionally attached, in data-communicative relationship, digital camera. The operator may then select the Donor History tab 251 (FIG.

2C) to view or modify procedure history data for this donor. This tab 251 may contain the following information: Blood Type, CMV, HLA, Hematocrit, or Platelet Count. More specifically, the Blood Type may include A+, A−, B+, B−, AB+, AB−, O+, O−, or Unknown; preferably accessible via a drop-down list, editable by selection only. Default is preferably "Unknown". The CMV Status includes Unknown, Positive, and Negative options. The default is preferably "Unknown". The operator may select the HLA Tested check box if HLA testing has been done for this donor. The HLA Tested check box is left unchecked by default. The A, B, C, D check boxes are disabled unless the HLA Tested check box is selected. Once HLA Tested is selected, the operator can select one or more HLA-type check boxes (A, B, C, or D). The Last Hematocrit and the Last Platelet Count are preferably non-editable, generally pre-populated fields from past procedure data or external blood bank information system, if available.

The operator may then also select the Comments tab 261 to enter or view free-form comments about the donor. To add a comment, the operator clicks an Add Comment button. A separate Enter Donor Comment pop-up dialog box (not shown) may then appear, or comments may be made enter-able within a workspace. The operator may also select the Allergies tab 271 to enter or view donor allergies and associated comments.

The operator may select the Status tab 281 (FIG. 2D) to enter or view the following donor status information: Donor Status—Active or Inactive; Donor Category (a drop-down list, preferably created by the System Administrator); Donor Since Date—date the donor started donating (preferably defaults to first procedure date, if not modified, which can be typed in text box or selected using a pop-up calendar); Last Visit Date—last date the donor attempted to donate (defaults from system records, preferably non-editable except by the System Administrator); Last Procedure Date—the last date the donor actually did donate (default from system records, non-editable except by the System Administrator); Last Contact Date—last date that the center contacted the donor (can be typed in text box or selected using pop-up calendar, default is preferably the current date).

The Blood Loss History tab 291 (FIG. 2E) shows the total volume of blood or particular blood components (for example, red blood cells or plasma) the donor has lost from apheresis activities for the previous 12-month period. The improvement of the present invention includes appropriate records for whole blood donations as well. All of the data in this tab is preferably non-editable in this module. It is downloaded as run data from the apheresis collection system 10 (preferably a Trima system 10) for procedures run for this donor, or entered by an operator during procedure finalization (see below). The tab 291 preferably shows the Total Blood Loss, the total volume (preferably in milliliters) of blood the donor has lost from apheresis and whole blood activities for the previous 12-month period; and a Procedure table which shows blood loss for apheresis procedures for which a procedure record exists in the assembly 140. Each procedure is preferably listed in a separate row in the table. The operator may need to scroll horizontally or vertically to view some of the data.

For each procedure, the table may show the following types of data. Procedure Date is the date the procedure was run. Product RBC is the volume of RBC product collected during the procedure (total RBC volume less anticoagulant volume). This information is preferably determined based on the procedure that was run and the donor's hematocrit. Sample RBC is the volume of sample RBCs collected during the procedure. This volume is either the default value set by the Administrator during system setup or a value entered by an operator during procedure finalization, according to the facility's SOPs. Residual RBC is the volume of residual RBCs remaining in the tubing set after the procedure. This information is determined based on the tubing set type, the procedure that was run, the donor's hematocrit, and whether or not rinseback was completed for the procedure. Other RBC is any other RBC volume (for example, estimated volume of a spill), entered by the operator in the Finalize Procedure Information dialog box, Blood Loss tab, according to the facility's SOPs. Product Plasma is the volume of plasma product collected during the procedure (total plasma volume less anticoagulant volume). The information is determined based on the procedure that was run and the donor's hematocrit. Sample Plasma (not shown) is the volume of sample plasma collected during the procedure. This volume is either the default value set by the Administrator during system setup, or a value entered by an operator during procedure finalization, according to the facility's SOP's. Residual Plasma (not shown) is the volume of residual plasma remaining in the tubing set after the procedure. This information is determined based on the tubing set type, the procedure that was run, the donor's hematocrit, and whether or not rinseback was completed for the procedure. Other Plasma (not shown) is any other plasma volume (for example, estimated volume of a spill), entered by the operator in the Finalize Procedure Information dialog box, Blood Loss tab, according to the facility's SOPs.

The operator may select the Procedure History tab 299 (FIG. 2F) to view product information for all procedures run for this donor since the donor record was created in the present assembly 140. The tab 299 shows product information preferably only for apheresis procedures for which a procedure record exists in the database 142. All of the data in this tab is preferably non-editable. It is downloaded from the apheresis system (preferably a Trima system) 10 run data for procedures run for this donor. The operator may need to scroll horizontally or vertically to view some of the data. For each procedure, this tab 299 preferably shows the following types of data. Procedure Date is the date the procedure was run. Platelet Yield is the yield of platelets collected during the procedure. Plasma Volume is the volume of plasma collected during the procedure (plasma product volume plus anticoagulant volume). RBC Volume is the volume of RBCs collected during the procedure (RBC product volume plus anticoagulant volume).

Various alternative data entry or editing actions may also be preferred. For example, at any time while using the Donor Entry dialog box 221, the operator may click the Apply button 229 to save changes to the donor record, without exiting the dialog box. Chacking an "Okay" button 230 saves changes to the donor record and exits the dialog box. Similarly, at any time while using the Donor Entry dialog box 221, the operator may click the Cancel button 228 to cancel the current entry session. The assembly 140 may then prompt the operator to confirm the cancellation. If cancellation is confirmed, the system may lose all unsaved changes and closes the Donor Entry dialog box 221. A Help button 227 is preferably also provided to present a corresponding help screen (not shown) when desired.

Figure 3A:
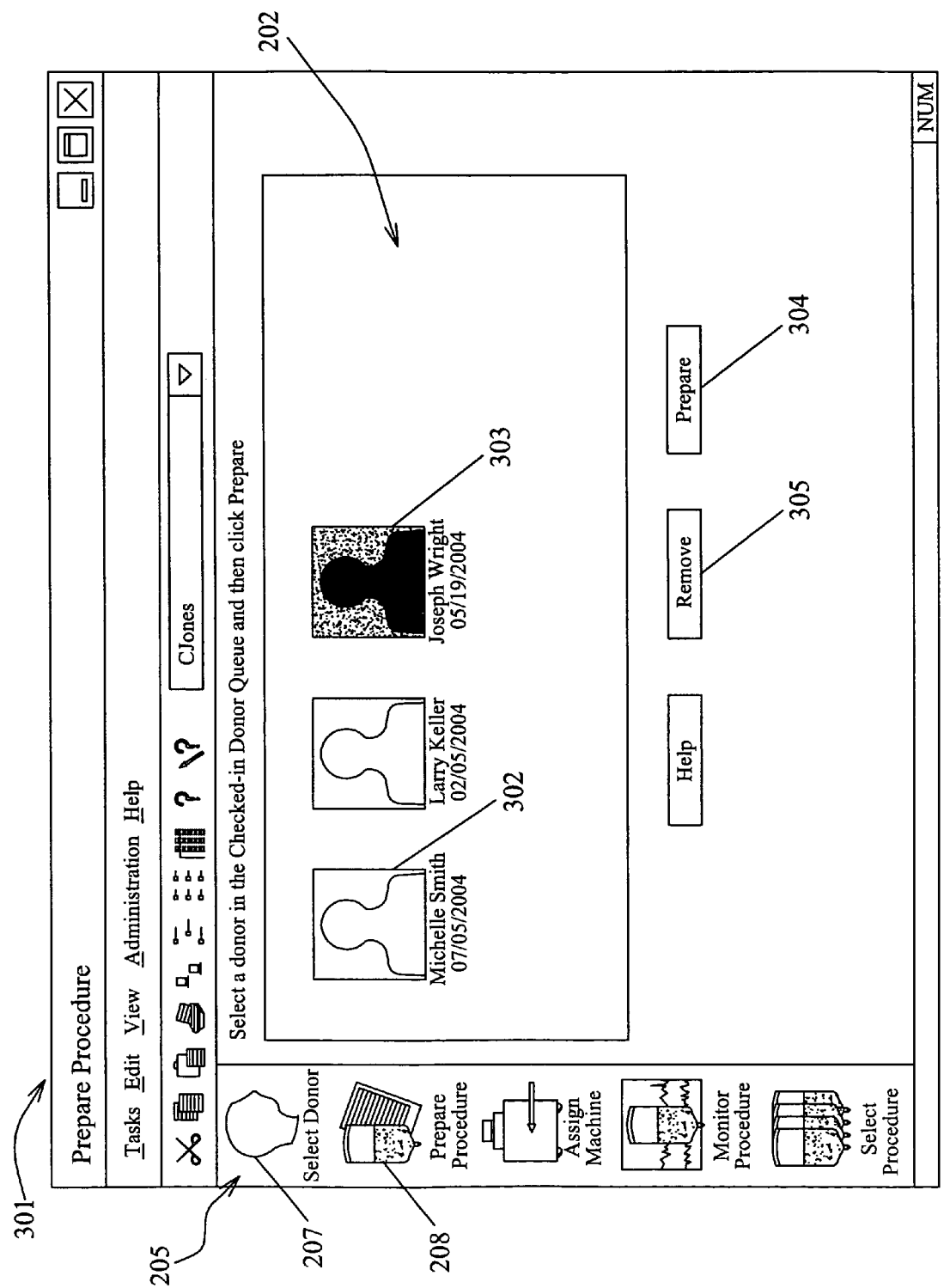
FIGS. 3A-3D are further display screen depictions of data entry, retrieval or manipulation display pages for use in accordance with the present invention.

FIG. 3A shows the next step in the collection procedure after donor check-in is completed. The display screen 301 shows the donors who have been checked into the system and are now ready for selection of the desired collection procedures. The work area 202 of screen 301 in FIG. 3A displays a listing of donors who have been checked-in. A donor may be selected by clicking the corresponding icon 302 or 303, for example. Once the donor is selected in screen 301, the next step can be accessed by clicking the "Prepare" button 304 in the main work area 202, or by again clicking the "Prepare Procedure" icon 208 in the icon area 205. A "Remove" button 305 could alternatively be selected to remove the donor, if desired.

In particular, screens 321, 331, and 351 represent screens accessed initially by the selection of the "Prepare" button 304 of screen 301 in FIG. 3A. These screens are accessed by the selection of the respective "Next" buttons 322 (see lower portions of screens in FIGS. 3B and 3C, e.g.). Backtracking is also available by selection of "Back" buttons 323.

Figure 3B:
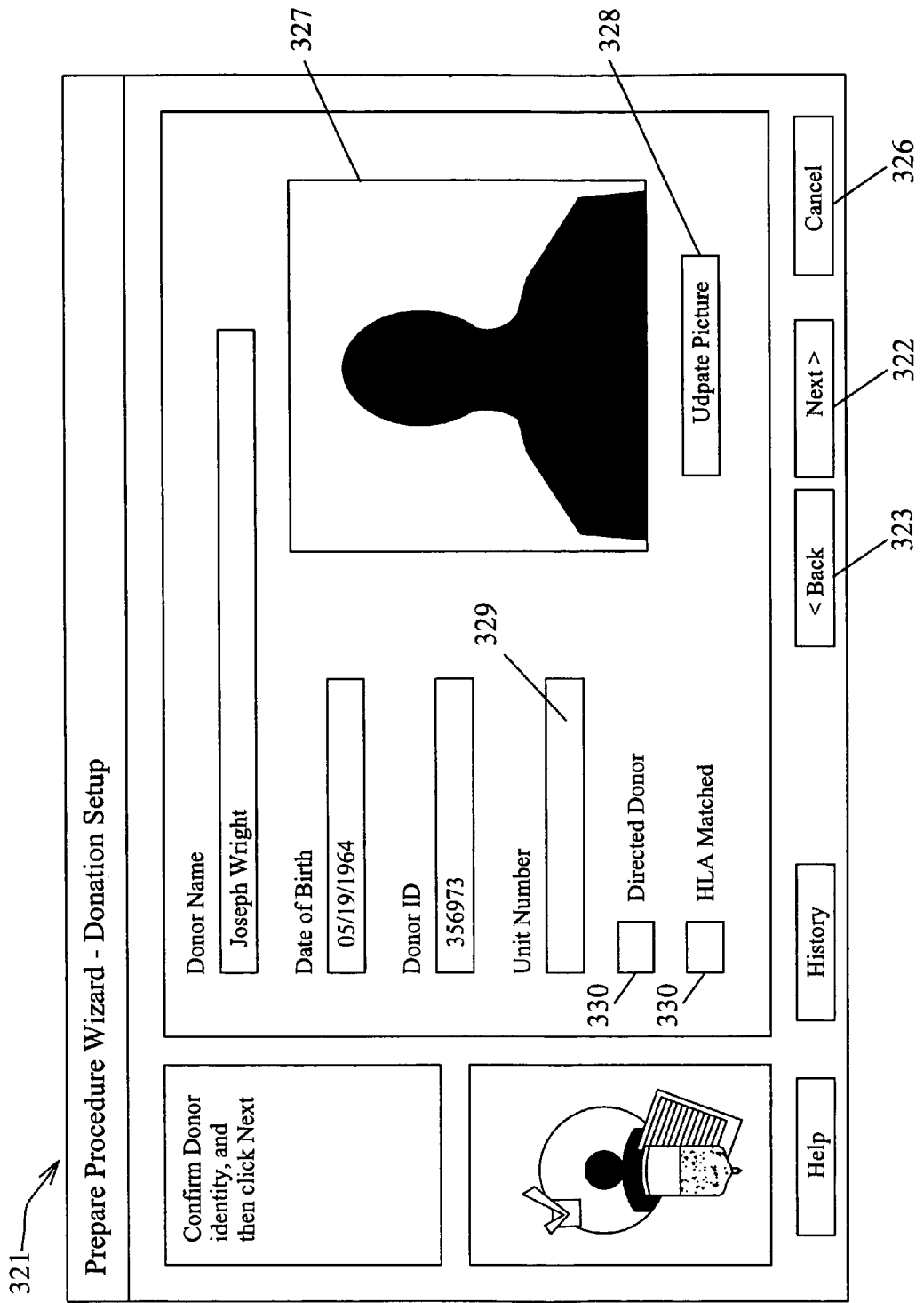

A Donation Set-up Screen 321, as shown in FIG. 3B, shows the donor's name, donor ID, date of birth (DOB), and photo 327. This page allows the operator to confirm the donor's identity and, optionally, to take or update 328 a photo 327 of the donor. Donor Name, Donor ID, Date of Birth, Donor's photo are pre-populated from the donor data entry sub-procedure described above.

A Unit Number text box 329 may also be disposed on screen 321. A Unit Number is preferably a required field entry. The operator may enter the unit number either by typing the number in the Unit Number box 329, or by using a barcode reader. The unit number may be supplies-related information such as the tubing set type used, or the bag types used. The Directed Donor and HLA matched boxes 330 are directed to noting whether this donor is directing a donation to a specific recipient, and whether the HLA types have already been matched for such a directed donation per pre-existing techniques.

Figure 3C:
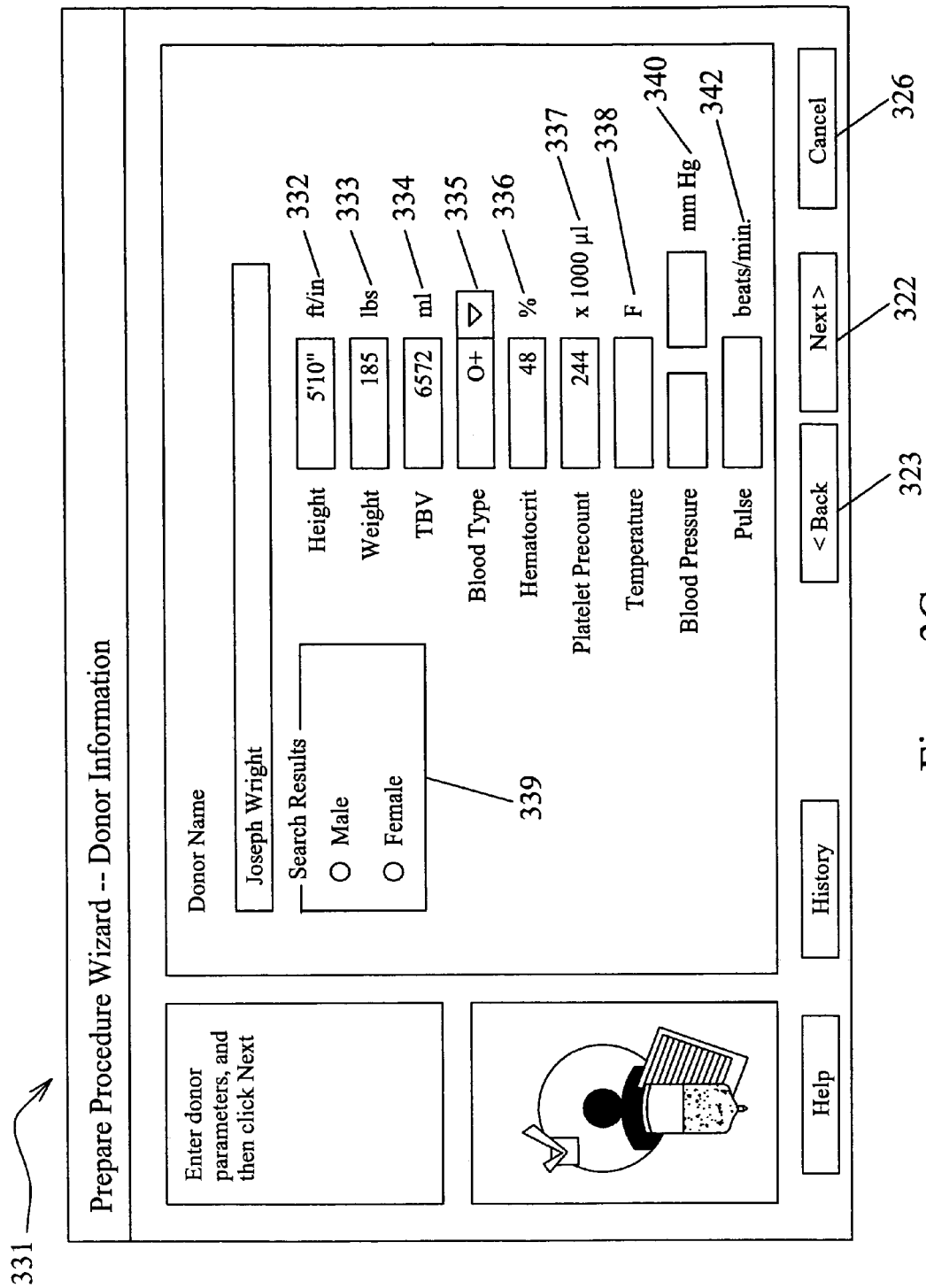

As shown by the display screen 331 in FIG. 3C, gender 339, height 332, weight 333 hematocrit 336, and platelet pre-count 337 parameters will be entered, if not already pre-populated in the respective fields from data previously entered in the database 142. Even if these parameters are previously entered, these fields in this screen 331 may be re-confirmed before the assembly 140 allows the operator or donation process to proceed. The other fields shown in this FIG. 3C (temperature 338, blood pressure 340, and pulse 342) are preferably entered as well, but may be optional. The required fields may be populated with historical data until the current lab values are available.

The "TBV" (Total blood volume) in field 334 is dynamically calculated (non-editable), based on the Height, Weight, and Gender fields 332, 333, 339. The Donor Blood type is also preferably pre-populated in field 335, either from database 142 or (if unknown for this donor) pre-populated with Unknown.

The Hematocrit/Hemoglobin field 336 is labeled either Hematocrit as shown or Hemoglobin (not shown), based on the system setup that is defined by the System Administrator. Data in this field is required, and may be entered by the operator, or a default value may exist. If the Administrator configures this field to use a default value, and historical data of the configured type is available for this donor, the field is pre-populated with the historical data. The type of historical data used as the default may be configured by the Administrator to be one of the following types: Average of last three pre-procedure values; Last visit's pre-procedure value; No default value; Gender-based default value; or blood center chosen default value. The value written to the database and displayed on the page indicates if the value is one of the configurable defaults or if it is a measured value entered by the operator.

The Platelet Pre-count field 337 is also entered here. Data in this field 337 is required, and may be entered by the operator, or a default value may exist as defined by the Administrator. If the Administrator configures this field to use a default value, and historical data of the configured type is available for this donor, the field is pre-populated with the historical data. The type of historical data which may be used as the default may be configured by the Administrator to be one of the following types: Average of last three pre-procedure values; Last visit's pre-procedure value; No default value; Gender or Center-wide default. The value written to the database and displayed on the page preferably indicates if the value is one of the configurable defaults or if it is a measured value entered by the operator. In other fields, the operator may enter the appropriate optional donor Temperature 338, Blood pressure 340, and Pulse 342.

When all required and optional information has been entered, the operator clicks the Next button 322 to proceed to the next page. If a required field does not have an entered value, an attempted click of the Next button 322 will preferably present a prompt that a value must be entered in this field. If the operator enters a value in a field that is above or below the allowable limits for that field (hard limits), or a value that is unusually high or unusually low (soft limits), a message will appear. If this is a soft limit, the message informs the operator that the value is outside the limits and asks if the operator wishes to proceed. The operator may click a Yes option to use the value and proceed, or No to enter a new value. If this is a hard limit, the operator may be required to enter a new value in order to proceed.

Figure 4:
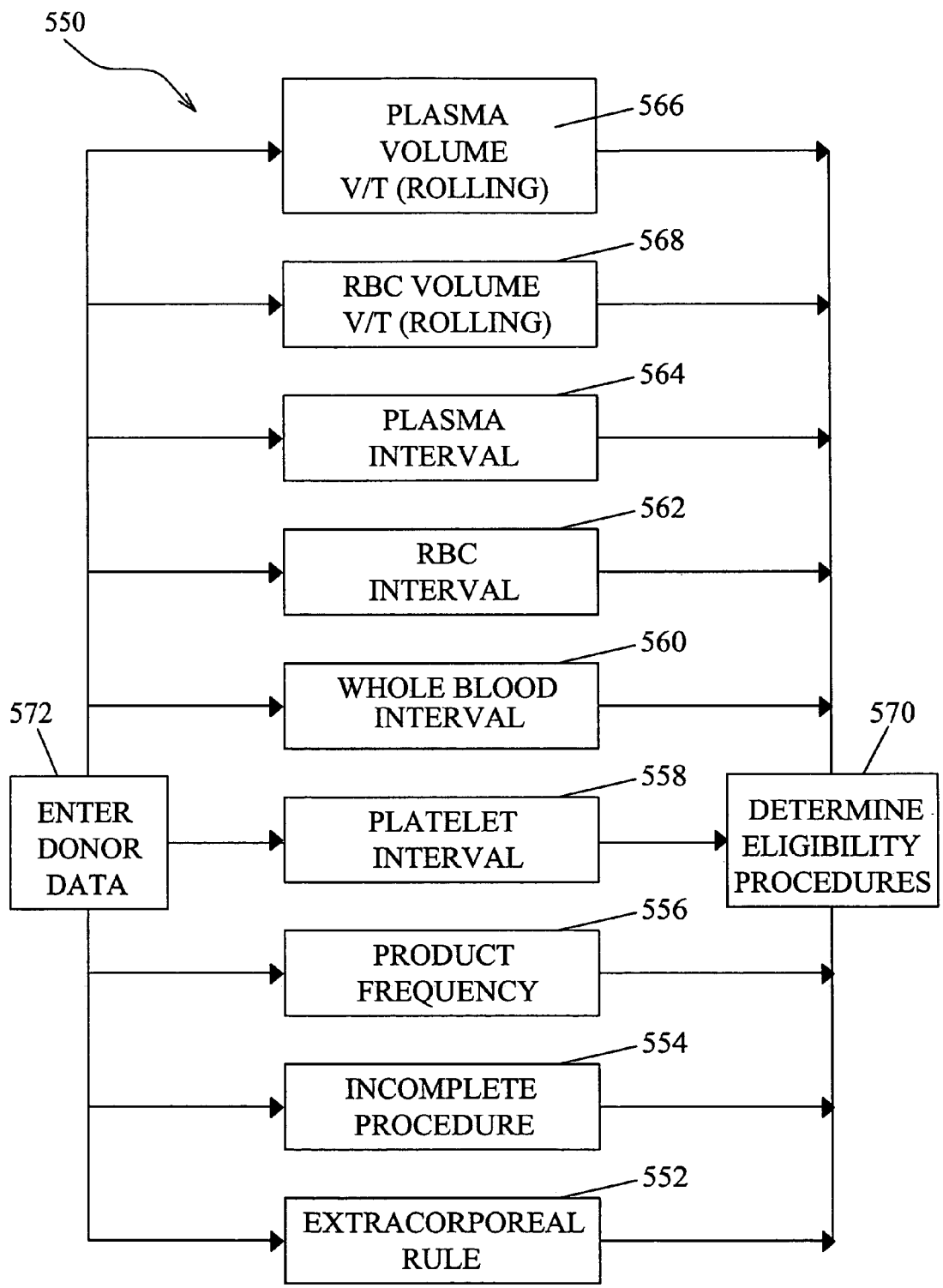
FIG. 4 is a schematic diagram of a decision tree for determining donor eligibility for particular blood collection procedures.

An advantage of the automated information system described herein is the capability to apply numerous donor eligibility rules to a particular donor, correlate the possible procedures or types of blood products that the donor can provide, and select the procedure producing a product most likely to be needed by the blood bank. In particular, this invention provides for integrating donor eligibility rules for permissible blood loss resulting from both apheresis (blood component) and whole blood donations. As illustrated in FIG. 4, a decision tree 550 may incorporate numerous donor eligibility rules after donor data has been entered 572 in the system, as described above. These rules may be set by regulation or selected by the blood center personnel. The rules determine minimum qualifications for a donor and are dependant on the donor's physical characteristics, history of blood donation and characteristics of the apparatus used to collect the donation. For example, an extracorporeal rule 552 may be imposed which limits the maximum volume of blood or blood components that can be outside a donor's body at any time during a procedure. This volume depends on the physical characteristics of the donor and the type and amount of product being collected. It also depends on the characteristics of the blood collection device, since different devices require different volumes of blood for processing. A donor may be qualified under this rule to donate certain blood products on particular machines.

In apheresis blood donation, although it is intended that certain blood components be returned to the donor, one must assume that the apparatus fails at the time of maximum blood loss, and that all blood components collected or still in the apparatus would not be returned to the donor. The donor's health must not be compromised by such an occurrence. An incomplete procedure rule 554 must be applied to the intended donation.

A product frequency rule 556 specifies that a donor cannot give more than a certain number of blood product donations within a pre-selected period of time, for example within a year. This kind of rule usually includes all types of product donation types, such as whole blood, plasma, platelet, or red blood cell donations. Without regard to the different types of donations, or the volumes of blood product given in each donation, a donor is usually limited to a certain maximum number of annual donations. The time period is rolling, that is, it is a selected period preceding the date of the proposed donation.

Each of the possible blood products can be collected at different intervals. There are, therefore, a platelet interval rule 558, a whole blood interval rule 560, a red blood cell (RBC) interval rule 562, and a plasma interval rule 564. These intervals, during which the donor's body replenishes its blood supply, are measured from the date of the last donation to the date of the proposed donation. In general, intervals between whole blood donations are longer than for component donations. A donor may be qualified to donate platelets or plasma, even if the donor were not able to give a donation of red blood cells or whole blood on a particular date.

Plasma volume and red blood cell volume rules are central to blood loss equivalency tracking. The plasma volume rule 566 limits the total volume of plasma a donor can lose within a selected interval, for example, a year. Preferably, the interval is rolling, that is, it is a selected interval preceding the date of the proposed donation. A calendar interval might also be used. The total volume of plasma is the sum of all the plasma losses attributable to blood donation, or other blood loss, if known. In apheresis donations, identification of the plasma loss during any particular donation is relatively exact. Since apheresis extracts measurable quantities of blood components, most apheresis machines can provide an actual measurement of collected plasma. Residual amounts of plasma not returned to the donor either after normal termination of the apheresis procedure or after an incomplete procedure, wherein blood may be left in the blood processing tubing set, are functions of the particular apheresis machine. These residual amounts are, therefore, well-defined and can be added to the total plasma volume. If the donor also gives whole blood donations, however, the amount of plasma loss is not directly measured and may not be known exactly. Whole blood donations generally involve collection into a sterile bag and do not require a monitoring device such as an apheresis machine. The amount of whole blood actually collected, including samples for testing, must be entered into the blood processing information system. If the donor's actual hematocrit is known, the volume attributable to plasma can be calculated as the amount of blood collected times the quantity 1 minus the hematocrit. If the donor's actual hematocrit is not known, a blood bank-selected minimum hematocrit is used. This calculation gives the largest volume for plasma loss and represents a conservative approach to meeting the plasma volume rule. Similarly, when predicting whether a donor is qualified to give a whole blood donation of a particular volume, the predicted plasma loss is computed using the donor's actual hematocrit, if known, or the minimum hematocrit, if the actual hematocrit is not known. The donor's qualifications for donating other blood products by apheresis are calculated using the actual hematocrit of the donor, if known, and the characteristics of the selected apheresis machine, further assuming a worst-case situation for the donation. For example, the potential plasma loss might be calculated assuming that a plasma donation had been substantially completed but that blood components remaining in the tubing set could not be returned to the donor. Only if the donor qualified for donation under the most severe conditions would a donation be suggested. Similarly, if the actual hematocrit of the donor were not known, qualification for apheresis donation would be calculated using the pre-determined minimum hematocrit.

The red blood cell volume rule 568 is calculated in the same manner as the plasma volume rule 566, except that where the donor's hematocrit at the time of a whole blood donation is not known, a pre-determined maximum hematocrit is used to calculate the donor's loss of red blood cells either from the actual donation or for a predicted donation. As for the plasma volume rule 566, the red blood cell volume rule 568 limits the total volume of plasma a donor can lose within a selected interval, for example, a year. The interval is rolling, that is, it is a selected interval preceding the date of the proposed donation. The total volume of red blood cells is the sum of all the red blood cell losses attributable to blood donation, or other blood loss, if known. In apheresis donations, identification of the red blood cell loss during any particular donation is relatively exact. Since apheresis extracts measurable quantities of blood components, most apheresis machines can provide an actual measurement of collected red blood cells. Residual amounts of red blood cells not returned to the donor either after normal termination of the apheresis procedure or after an incomplete procedure, wherein blood may be left in the blood processing tubing set, are functions of the particular apheresis machine. These residual amounts are, therefore, well-defined and can be added to the total red blood cell volume. As in the case of plasma, above, if the donor also gives whole blood donations, the amount of red blood cell loss is not directly measured and may not be known exactly. Once again, the amount of whole blood actually collected, including samples for testing, must be entered into the blood processing information system. Only one such data entry is required, of course, for the calculation of both plasma and red blood cell losses. If the donor's actual hematocrit is known, the volume attributable to red blood cells can be calculated as the hematocrit times the amount of blood collected. If the donor's actual hematocrit is not known, a blood bank-selected maximum hematocrit is used. This calculation gives the largest volume for red blood cell loss and represents a conservative approach to meeting the red blood cell volume rule. Similarly, when predicting whether a donor is qualified to give a whole blood donation of a particular volume, the predicted red blood cell loss is computed using the donor's actual hematocrit, if known, or the maximum hematocrit, if the actual hematocrit is not known. The donor's qualifications for donating other blood products by apheresis are calculated using the actual hematocrit of the donor, if known, and the characteristics of the selected apheresis machine, further assuming a worst-case situation for the donation. For example, the potential red blood cell loss might be calculated assuming that a red blood cell donation had been substantially completed but that blood components remaining in the tubing set could not be returned to the donor. Only if the donor qualified for donation under the most severe conditions would a donation be suggested. Similarly, if the actual hematocrit of the donor were not known, qualification for apheresis donation would be calculated using the pre-determined maximum hematocrit.

Once the desired donor data is satisfactorily entered, edited or verified using screen 221, the donor may then be checked-in to the next step in the process, the Prepare Procedure step. The blood processing information system will only allow or suggest procedures 570 for which the donor is qualified in view of the donor qualification rules 552-568 described above. The Prepare Procedure donor check-in step may be accomplished from any view of screen 221 by clicking the "OK" button 230. This may then send the donor information to the Prepare Procedure portion of the software application (e.g., from the Donor Check-in module to the Prepare Procedure software module, if the software is modulized as is preferred). Alternatively, a pop-up dialog box (not shown) can be made to appear for confirmation that donor check-in is desired. "Yes" or "No" options may be provided in such a pop-up dialog box to confirm the operator's desires. Clicking the "Yes" option will then pass the donor information to the Prepare Procedure Step, as described. Clicking the "No" option will not pass the donor information to the next procedural step. The operator may return to screen 221 at later stages of the procedure to enter new data or modify existing data.

Figure 3D:
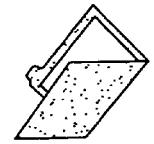

On the Target Procedure page 351, the operator may accept the recommended target procedure (shown with a rightward-pointing arrow icon 355 in FIG. 3D). The target procedure is selected by the assembly 140 running the apheresis time or product yield optimization routines as are known from the Trima® apheresis machines 10 or as described in U.S. Pat. Nos. 5,496,265; 5,658,240; 5,712,798; and 5,970,423, all of which being commonly assigned to the assignee of the present invention, the disclosures of which being incorporated herein in their entireties as if fully set forth here by this reference thereto. The parameters for the highlighted procedure are preferably shown above the procedure list. The operator may click the Finish button 352 to complete the "Prepare Procedure" selection process.

The assembly 140 and manipulation device 144 can compare the characteristics of a donor against many procedure types and blood center priorities to obtain procedure lists such as that shown in FIG. 3D. The optimal procedure is returned with the rightward-pointing arrow icon 355. Other procedures will also be listed with various icon representations to signify prioritization. For example, procedures shown with a circle with a diagonal line (red in color) are not available due to physical or safety constraints such as the donor not meeting a minimum hematocrit or total blood volume. Open circles (green in color) signify less than optimal procedures, which are nevertheless available for this donor. Question marks (yellow in color) signify procedures, which could be available options if one or more parameters (e.g., time) were to change (e.g., if more time were allowed for a collection).

More than one target procedure may be indicated, and the operator may choose the preferred procedure. Or the donor may be disqualified such that no procedures appear available. The donor can be disqualified for the donation based on the donor vitals or screening questions. In this situation, the operator may press the Cancel button 326 to discontinue the Prepare Procedure process. The operator may then remove the donor from Checked-in Donor status.

An operator may select different donation procedure configuration options, preferably after the donor "vitals" step depicted by screen 331 (FIG. 3C), but prior to the optimization step depicted by screen 351 (FIG. 3D). Then an additional page may appear, allowing finer control of the donation. The operator would choose the blood product types eligible for this donation (e.g. platelets, RBC's or plasma). These choices would be used to disqualify one or more product types from being collected. By default, all product types are preferably eligible for a donation. The preferred three choices are platelets, plasma and red blood cells. Any combination hereof may be checked. The operator may also select alternative apheresis system configurations or product focus lists to utilize for this particular donor's donation. These changes would preferably only apply to this particular donation.

After a donation has been collected, the operator collects final data through a Finalize Information Screen 621. For example, the operator may view a Run Summary 681 (FIG. 5A). The apheresis machine 10 provides product volume information after the run is complete. Until the procedure is completed, all of the fields in this screen are blank. The information would then be non-editable and defaulted from the procedure run data (machine run summary). This information preferably includes the following: the estimated volume for platelet, plasma and RBC products; the AC volume in platelet, plasma and RBC products; the estimated yield for platelet products; the total AC volume used; the AC administered to the donor during the procedure; the total blood volume processed; and Summary remarks, preferably including one or more of the following: a reminder to label LRS platelet product as having less than $1 \times 10e6$ white blood cells (if leukoreduced, as on the Trima® system 10); a reminder to count the product; a reminder to verify platelet yield; a reminder to verify platelet volume; a reminder to determine whether platelet concentration is out of range; a reminder to verify plasma volume; and a reminder to verify RBC product.

The operator may also view a Blood Loss screen 691 (FIG. 5B) to view blood loss entries. Blood loss information preferably includes the Product, the Tubing Set Residual, the Blood Sample and an Other column. A check box for Rinseback Completion is also provided. In more detail, the Product column shows product volume for plasma and RBCs. This information is preferably downloaded from the apheresis system 10 run data for this procedure, and is preferably non-editable. The information is determined based on the procedure that was run and the donor's hematocrit. Until the procedure is completed, these fields are blank. The Tubing Set Residual preferably shows the volume of plasma and RBCs remaining in the tubing set. This information is also preferably downloaded from the apheresis system run data for this procedure, and is preferably non-editable. During the procedure, this information is determined based on the collection status, the tubing set type, the procedure that is being run, and the donor's hematocrit. When the procedure is completed, this information is determined based on all of the above, as well as whether or not rinseback was completed for the procedure. The Blood Sample column presents the volume of blood, entered by operator for plasma or RBCs, according to the facility's SOPs. The Administrator specifies the default value, if used. The Other column includes any Other volume of blood (for example, estimated volume of a spill), entered by operator for plasma or RBCs, according to the facility's SOPs. The Donor Completed Rinseback check box is checked if rinseback was completed for the procedure. Until the procedure is completed, this box remains unchecked. This information is also preferably downloaded from the apheresis system run data for this procedure, and is preferably non-editable.

After entering the data required by the SOP's of a particular blood center, the operator may then click the "OK" button 622 to save the record. The assembly 140 saves the procedure record. If all the required information has been entered, the assembly 140 updates the status of the record to be closed.

Donor recruitment or eligibility can be run by a centralized system to determine which donors may be able to provide certain products at a certain time. The data may be obtained by data input as above, or with data already existing in the database 142 or as may be obtained by communication with a discrete information system. Most preferably, these procedures could be performed without the specific potential donor present to predict what the donor could yield, and then if a desirable product is predicted (i.e., the potential donor is eligible or qualified to give the desired product or products), the potential donor could then be contacted to recruit them to undergo the procedure. In this fashion, a blood center could better tailor its blood and blood component supply to better match demand.

Notwithstanding the foregoing description of the present invention in relation to a blood component collection process, those skilled in the art will appreciate that the source of blood may be provided to the blood component collection device from an appropriate blood container (not shown) interconnected with the blood component collection device 18 versus receiving such directly from a human donor. Moreover, the blood of course may be provided from alternative sources such as animals. In addition, the present invention is applicable to the collection of whole blood as well as blood components such as red blood cells, stem cells, white blood cells, or plasma, and is further applicable to the simultaneous collection of more than one blood component type.

The foregoing description of the present invention has been presented for purposes of illustration and description. Although the preferred embodiment of the invention has been described in language which may be thought specific to structural features, methodological acts, and computer readable media containing such acts, it is rather intended to be understood that the invention defined in the appended claims is not necessarily limited to the specific structure, acts or media so described. The specific structure, acts or media are disclosed as preferred forms of implementing the claimed invention. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention, and such other embodiments, and with various modifications required by the particular applications or uses of the present invention. It is intended that the appended claims be construed to include alternative embodiments to the extent permitted by the prior art.

What is claimed is:

1. An extracorporeal blood processing information management system comprising:
    a central database;
    a data input device;
    a data manipulation device connected in data communication relationship with at least one of said central database and said data input device; and
    a communication subsystem connected in data communication relationship with said central database and said data manipulation device; and
    said central database maintaining records of total donation volumes contributed by a donor, said donation volumes being volumes of fluid not returned to said donor, said records being maintained for a plurality of donations by said donor during selected time periods as communicated by said blood processing machine and as determined by said data manipulation device, said records comprising a total red blood cell donation volume and a total plasma donation volume for said plurality of donations.

2. The extracorporeal blood processing information management system of claim 1 wherein said total red blood cell donation volume comprises at least one actual red blood cell donation volume and at least one calculated red blood cell donation volume and at least one estimated red blood cell donation volume.

3. The extracorporeal blood processing information management system of claim 2 wherein said calculated red blood cell donation volume comprises an actual whole blood donation volume reduced according to a known donor hematocrit.

4. The extracorporeal blood processing information management system of claim 3 wherein said estimated red blood donation volume comprises an actual whole blood donation volume reduced according to a maximum hematocrit.

5. The extracorporeal blood processing information management system of claim 2 wherein said estimated red blood donation volume comprises an actual whole blood donation volume reduced according to a maximum hematocrit.

6. The extracorporeal blood processing information management system of claim 1 wherein said total plasma donation volume comprises at least one actual plasma donation volume and at least one calculated plasma donation volume and at least one estimated plasma donation volume.

7. The extracorporeal blood processing information management system of claim 6 wherein said calculated plasma donation volume comprises an actual whole blood donation volume reduced according to a known donor hematocrit.

8. The extracorporeal blood processing information management system of claim 7 wherein said estimated plasma donation volume comprises an actual whole blood donation volume reduced according to a minimum hematocrit.

9. The extracorporeal blood processing information management system of claim 6 wherein said estimated plasma donation volume comprises an actual whole blood donation volume reduced according to a minimum hematocrit.

10. The extracorporeal blood processing information management system of claim 9 wherein said estimated red blood donation volume comprises an actual whole blood donation volume reduced according to a maximum hematocrit.

11. The extracorporeal blood processing information management system of claim 10 wherein said calculated red blood cell donation volume comprises an actual whole blood donation volume reduced according to a known patient hematocrit and wherein said calculated plasma donation volume comprises an actual whole blood donation volume reduced according to a known donor hematocrit.

12. The extracorporeal blood processing information management system of claim 1 further comprising at least one extracorporeal blood processing machine in data communication relationship with said communication subsystem, said blood processing machine being capable of communicating data concerning a donation volume contributed by a donor.

13. An extracorporeal blood processing information management system comprising:
    a central database; and
    means for creating records of total donation volumes contributed by a donor, said donation volumes being volumes of fluid not returned to said donor, said records being maintained for a plurality of donations by said donor during selected time periods as communicated by said blood processing machine and as determined by said data manipulation device, said records being stored in said central database and comprising a total red blood cell donation volume and a total plasma donation volume for said plurality of donations.

14. The extracorporeal blood processing information management system of claim 13 wherein said total red blood cell donation volume comprises at least one actual red blood cell donation volume and at least one calculated red blood cell donation volume and at least one estimated red blood cell donation volume.

15. The extracorporeal blood processing information management system of claim 14 further comprising means for determining said calculated red blood cell donation volume from an actual whole blood donation volume reduced according to a known donor hematocrit.

16. The extracorporeal blood processing information management system of claim 15 further comprising means for determining said estimated red blood donation volume from an actual whole blood donation volume reduced according to a maximum hematocrit.

17. The extracorporeal blood processing information management system of claim 14 further comprising means for determining said estimated red blood donation volume comprises an actual whole blood donation volume reduced according to a maximum hematocrit.

18. The extracorporeal blood processing information management system of claim 13 further comprising means for determining said total plasma donation volume from at least one actual plasma donation volume and at least one calculated plasma donation volume and at least one estimated plasma donation volume.

19. The extracorporeal blood processing information management system of claim 18 further comprising means for determining said calculated plasma donation volume from an actual whole blood donation volume reduced according to a known donor hematocrit.

20. The extracorporeal blood processing information management system of claim 19 further comprising means for determining said estimated plasma donation volume from an actual whole blood donation volume reduced according to a minimum hematocrit.

21. The extracorporeal blood processing information management system of claim 18 further comprising means for determining said estimated plasma donation volume from an actual whole blood donation volume reduced according to a minimum hematocrit.

22. The extracorporeal blood processing information management system of claim 21 further comprising means for determining said estimated red blood donation volume from an actual whole blood donation volume reduced according to a maximum hematocrit.

23. The extracorporeal blood processing information management system of claim 22 further comprising means for determining said calculated red blood cell donation volume from an actual whole blood donation volume reduced according to a known patient hematocrit and further comprising means for determining said calculated plasma donation volume from an actual whole blood donation volume reduced according to a known donor hematocrit.

24. The extracorporeal blood processing information management system of claim 13, further comprising at least one extracorporeal blood processing machine in data communication relationship with said central database, said blood processing machine being capable of communicating data concerning a donation volume contributed by a donor.

25. A method for determining eligibility of a blood donor, the method comprising:
providing a central database; and
creating records of total donation volumes contributed by a donor, said donation volumes being volumes of fluid not returned to said donor, said records being maintained for a plurality of donations by said donor during selected time periods as communicated by said blood processing machine, said records comprising a total red blood cell donation volume and a total plasma donation volume for said plurality of donations, and
storing said in said central database.

26. The method of claim 25 wherein said total red blood cell donation volume comprises at least one actual red blood cell donation volume and at least one calculated red blood cell donation volume and at least one estimated red blood cell donation volume.

27. The method of claim 26 further comprising determining said calculated red blood cell donation volume from an actual whole blood donation volume reduced according to a known donor hematocrit.

28. The method of claim 27 further comprising determining said estimated red blood donation volume from an actual whole blood donation volume reduced according to a maximum hematocrit.

29. The method of claim 26 further comprising determining said estimated red blood donation volume comprises an actual whole blood donation volume reduced according to a maximum hematocrit.

30. The method of claim 25 further comprising determining said total plasma donation volume from at least one actual plasma donation volume and at least one calculated plasma donation volume and at least one estimated plasma donation volume.

31. The method of claim 30 further comprising determining said calculated plasma donation volume from an actual whole blood donation volume reduced according to a known donor hematocrit.

32. The method of claim 31 further comprising determining said estimated plasma donation volume from an actual whole blood donation volume reduced according to a minimum hematocrit.

33. The method of claim 30 further comprising determining said estimated plasma donation volume from an actual whole blood donation volume reduced according to a minimum hematocrit.

34. The method of claim 33 further comprising determining said estimated red blood donation volume from an actual whole blood donation volume reduced according to a maximum hematocrit.

35. The method of claim 34 further comprising determining said calculated red blood cell donation volume from an actual whole blood donation volume reduced according to a known patient hematocrit and determining said calculated plasma donation volume from an actual whole blood donation volume reduced according to a known donor hematocrit.

36. The method of claim 25 further comprising communicating data concerning a donation volume contributed by a donor from at least one extracorporeal blood processing machine in data communication relationship with said central database.

* * * * *